(12) United States Patent
Ochi et al.

(10) Patent No.: US 9,157,881 B2
(45) Date of Patent: Oct. 13, 2015

(54) ORGANISM SAMPLE MEASUREMENT SENSOR AND HOUSING CONTAINER THAT HOUSES SAME

(75) Inventors: Hirotaka Ochi, Ehime (JP); Masumi Aono, Ehime (JP)

(73) Assignee: PANASONIC HEALTHCARE HOLDINGS CO., LTD., Tokyo (JP)

( * ) Notice: Subject to any disclaimer, the term of this patent is extended or adjusted under 35 U.S.C. 154(b) by 153 days.

(21) Appl. No.: 14/116,389

(22) PCT Filed: May 16, 2012

(86) PCT No.: PCT/JP2012/003180
§ 371 (c)(1),
(2), (4) Date: Nov. 8, 2013

(87) PCT Pub. No.: WO2012/157262
PCT Pub. Date: Nov. 22, 2012

(65) Prior Publication Data
US 2014/0083849 A1    Mar. 27, 2014

(30) Foreign Application Priority Data

May 16, 2011 (JP) ................................ 2011-109037
Jun. 7, 2011 (JP) ................................ 2011-126987

(51) Int. Cl.
| | | |
|---|---|---|
| *G01N 27/327* | (2006.01) | |
| *G01N 27/30* | (2006.01) | |
| *A61B 19/02* | (2006.01) | |
| *G01N 1/00* | (2006.01) | |
| *G01N 33/487* | (2006.01) | |
| *B01L 3/00* | (2006.01) | |

(52) U.S. Cl.
CPC ............ *G01N 27/307* (2013.01); *A61B 19/026* (2013.01); *G01N 1/00* (2013.01); *G01N 27/327* (2013.01); *G01N 33/4875* (2013.01); *B01L 3/00* (2013.01)

(58) Field of Classification Search
None
See application file for complete search history.

(56) References Cited

U.S. PATENT DOCUMENTS

2008/0011605 A1    1/2008  Kusaka
2012/0080330 A1*   4/2012  Rush et al. ................. 206/305
(Continued)

FOREIGN PATENT DOCUMENTS

| JP | 08-267970 A | 10/1996 |
| JP | 2006-188255 A | 7/2006 |
| JP | 2010-038885 A | 2/2010 |
| JP | 2010-173674 A | 8/2010 |

(Continued)

OTHER PUBLICATIONS

International Search Report for Application No. PCT/JP2012/003180 dated Jul. 3, 2012.

*Primary Examiner* — Jennifer Dieterle
(74) *Attorney, Agent, or Firm* — Pearne & Gordon LLP

(57) ABSTRACT

The present invention is provided with sensor body (2) having a long plate shape, measurement part (3) provided in a front end section of sensor body (2), and connection terminal (4) provided in a rear end section of sensor body (2). Close contact prevention parts (10) having the same plate shape are provided in the same position of both a front surface and a back surface of sensor body (2), the position not overlapping with a position of a center of gravity of sensor body (2), measurement part (3), and connection terminal (4). A length in a longitudinal direction of sensor body (2) of close contact prevention parts (10) is shorter than a length thereof orthogonal to the longitudinal direction.

17 Claims, 12 Drawing Sheets

(56) References Cited

U.S. PATENT DOCUMENTS

2012/0082597 A1* 4/2012 Doniger et al. ............... 422/401
2013/0168276 A1* 7/2013 Shinno et al. ................. 206/370

FOREIGN PATENT DOCUMENTS

| | | |
|---|---|---|
| JP | 2010-217074 A | 9/2010 |
| WO | 2005/103663 A1 | 11/2005 |

* cited by examiner

CENTER OF GRAVITY

ORGANISM SAMPLE MEASUREMENT SENSOR AND HOUSING CONTAINER THAT HOUSES SAME

TECHNICAL FIELD

The present invention relates to an organism sample measurement sensor, such as a blood sugar level sensor, and a housing container that houses the same.

BACKGROUND ART

A configuration of a conventional organism sample measurement sensor, such as a blood sugar level sensor, is as follows.

That is, as shown in FIG. 15, conventional blood sugar level sensor 101 includes sensor body 102 having a long plate shape, measurement part 103 provided in a front end section of the sensor body, connection terminal 104 provided in a rear end section of the sensor body, and a connection part (not shown) connecting measurement part 103 and connection terminal 104. A plurality of blood sugar level sensors 101 are housed in a housing container having a bottomed cylindrical shape (for instance, see Patent Literature 1).

However, the conventional organism sample measurement sensor and the housing container that houses the same have very low convenience.

That is, blood sugar level sensor 101 as the conventional organism sample measurement sensor has sensor body 102 having a long plate shape, and as described above, a plurality of blood sugar level sensors 101 are housed in the housing container having a bottomed cylindrical shape (not shown) to be overlapped and in close contact with each other. It is difficult to draw blood sugar level sensors 101 that are overlapped and in close contact with each other out of the housing container one by one. Sometimes, a plurality of blood sugar level sensors 101 can be taken out to drop one or more of them.

Consequently, a user needs to slowly and carefully draw one blood sugar level sensor 101 out of the housing container. As a result, blood sugar level sensor 101 as the organism sample measurement sensor cannot be easily taken out of the housing container.

Accordingly, an object of the present invention is to easily take an organism sample measurement sensor out of a housing container.

CITATION LIST

Patent Literature

PTL 1: Unexamined Japanese Patent Publication No. 2010-173674

SUMMARY OF THE INVENTION

The present invention is provided with a sensor body having a long plate shape, a measurement part provided in a front end section of the sensor body, a connection terminal provided in a rear end section of the sensor body, and a connection part electrically connecting the measurement part and the connection terminal in the sensor body. Close contact prevention parts having the same plate shape are provided in the same position of both a front surface and a back surface of the sensor body, the position not overlapping with a position of a center of gravity of the sensor body, the measurement part, and the connection terminal. A length in a longitudinal direction of the sensor body of the close contact prevention parts is shorter than a length thereof orthogonal to the longitudinal direction.

This can easily take a sensor out of the housing container.

That is, in the present invention, the close contact prevention parts having substantially the same shape adhere into the same position of both the front surface and the back surface of the sensor body. Therefore, a plurality of blood sugar level sensors cannot come into close contact with each other in a housing container, and can be individually separated.

In addition, the close contact prevention parts are provided on the sensor body between the position of the center of gravity of the sensor body and the measurement part (that is, on a measurement part side). The sensor body is housed in the housing container so that the measurement part side is located toward an opening side of the housing container. Therefore, the close contact prevention parts on the sensor body are arranged near an opening in a top surface of the housing container.

Therefore, a user can insert e.g., his/her forefinger from the opening of the housing container to abut the inserted forefinger onto the close contact prevention parts near the opening.

As a result, only one of the individually separated sensors can be easily taken out of the housing container.

DESCRIPTION OF EMBODIMENTS

Hereinafter, an organism sample measurement sensor according to a first exemplary embodiment of the present invention applied to a blood sugar level sensor measuring a blood sugar level will be described with reference to the accompanying drawings.

First Exemplary Embodiment

Figure 1:
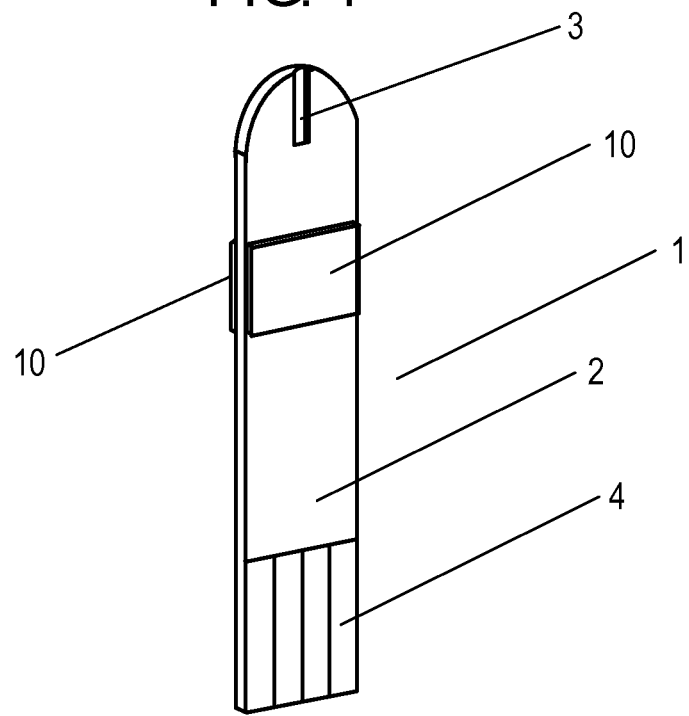
FIG. 1 is a perspective view of an organism sample measurement sensor according to a first exemplary embodiment of the present invention.
Figure 2:
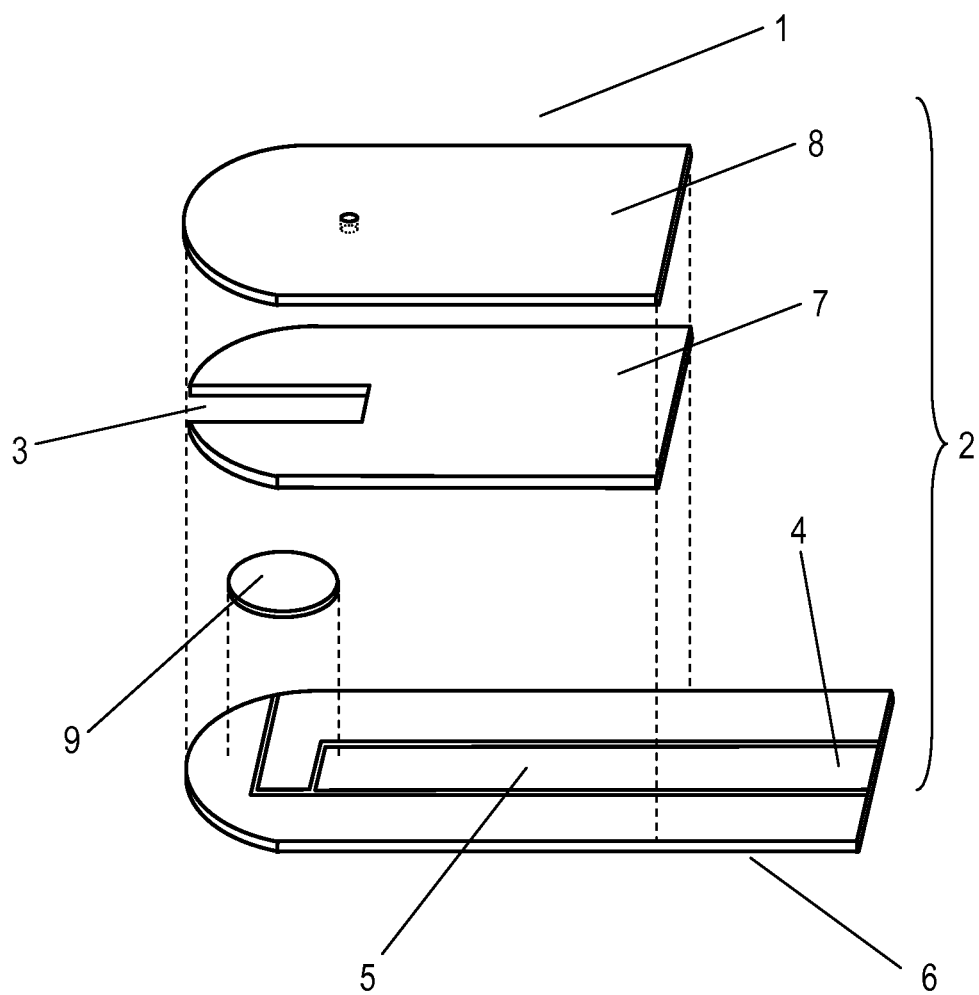
FIG. 2 is an exploded view of the organism sample measurement sensor according to the first exemplary embodiment of the present invention.

As shown in FIG. 1, blood sugar level sensor 1 as an organism sample measurement sensor includes sensor body 2 having a long plate shape, measurement part 3 provided in a front end section of sensor body 2, connection terminal 4 provided in a rear end section of sensor body 2, and connection part 5 shown in FIG. 2 and electrically connecting measurement part 3 and connection terminal 4 in sensor body 2.

As shown in FIG. 2, blood sugar level sensor 1 includes substrate 6, spacer 7, and cover 8 that are stacked and integrated. In addition, in measurement part 3 formed in spacer 7, reagent 9 is sandwiched between substrate 6 and spacer 7.

That is, as is well known, blood spotted onto measurement part 3 reacts with reagent 9 to change a terminal current of connection terminals 4 according to a blood sugar level in the blood. The terminal current corresponding to the blood sugar level is transmitted to a measurement device (not shown) via connection part 5 and connection terminal 4.

Figure 6:
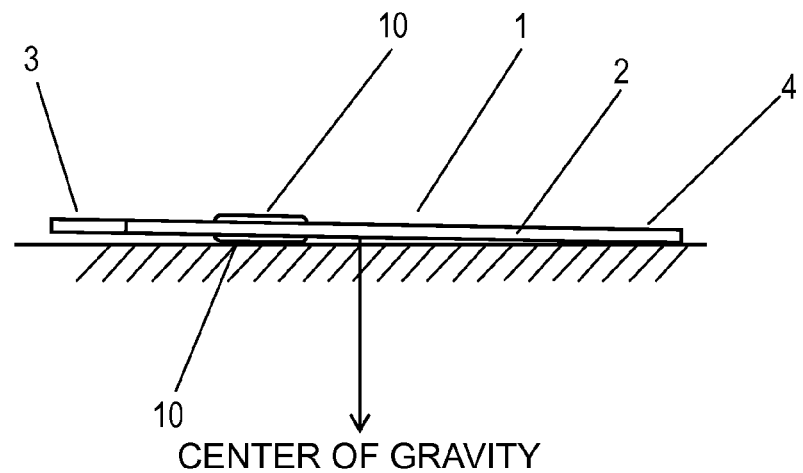
FIG. 6 is a side view of the organism sample measurement sensor according to the first exemplary embodiment of the present invention.

As shown in FIG. 1, in this exemplary embodiment, close contact prevention parts 10 having substantially the same plate shape are provided in the same position of both a front surface and a back surface of sensor body 2. Close contact prevention parts 10 are provided in a position between a position of a center of gravity of sensor body 2 and measurement part 3, the position not overlapping with the position of the center of gravity of sensor body 2 and measurement part 3. That is, as shown in FIG. 6, close contact prevention parts 10 are provided in the position between the position of the center of gravity of sensor body 2 and measurement part 3 in a state where blood sugar level sensor 1 is laid sideways, the position not overlapping with the position of the center of gravity of sensor body 2 and measurement part 3.

As shown in FIG. 1, a length in a longitudinal direction of sensor body 2 of close contact prevention parts 10 (a length in an up-down direction in FIG. 1) is shorter than a length thereof orthogonal to the longitudinal direction (a length in a right-left direction in FIG. 1). In addition, close contact prevention parts 10 are provided from a right end section of sensor body 2 to a left end section thereof in the direction orthogonal to the longitudinal direction of sensor body 2. That is, close contact prevention parts 10 are provided from end to end in a lateral direction of sensor body 2. In this way, close contact prevention parts 10 are made longer in the lateral direction of sensor body 2, and are made shorter in the longitudinal direction of sensor body 2. For instance, a length in the lateral direction of sensor body 2 is 6.5 mm, the length in the longitudinal direction of sensor body 2 of close contact prevention parts 10 is 4 mm.

Figure 3:
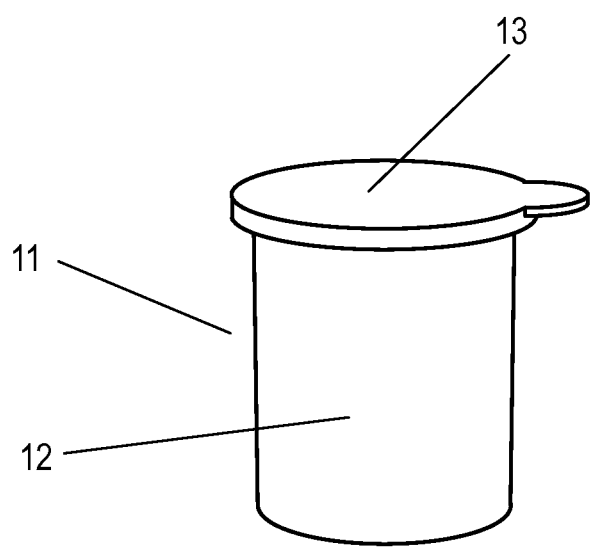
FIG. 3 is a perspective view of a housing container according to the first exemplary embodiment of the present invention.
Figure 4:
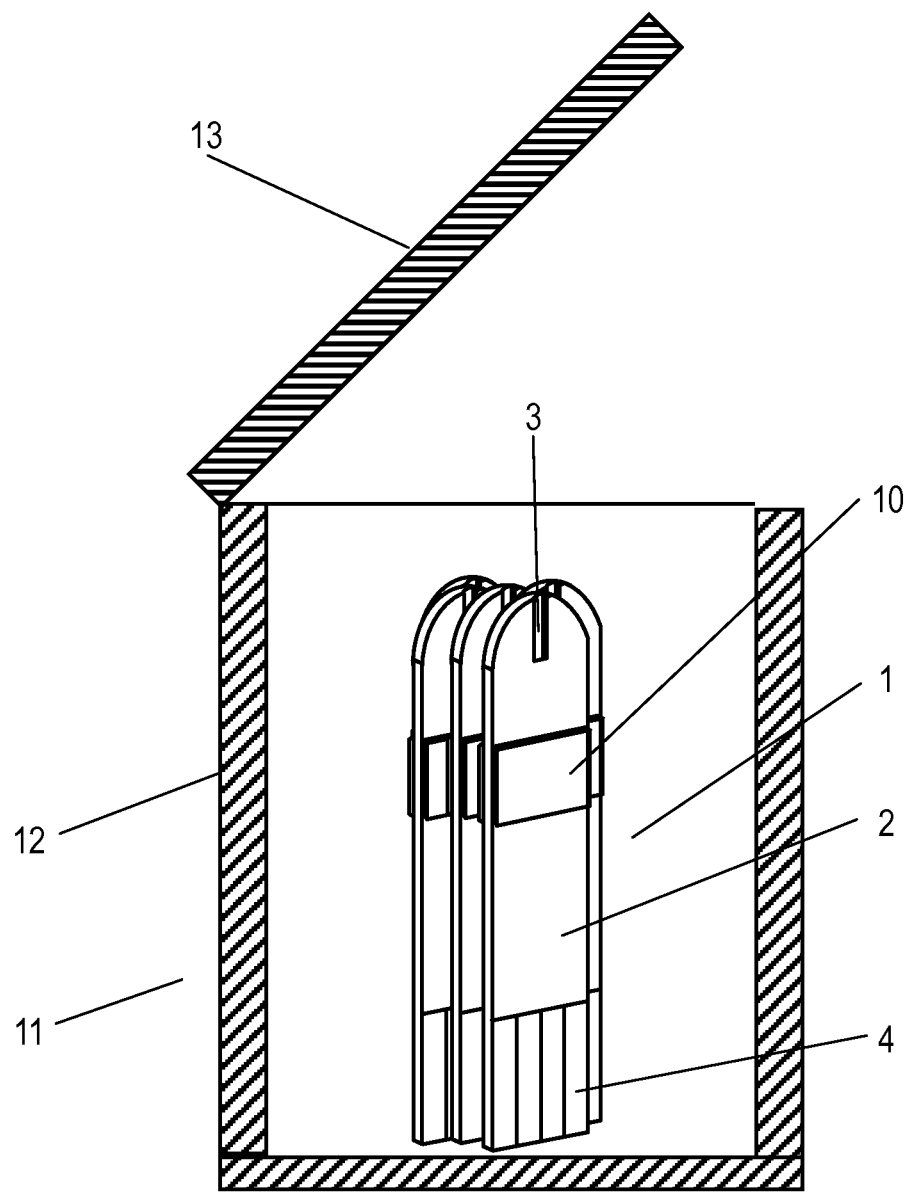
FIG. 4 is a cross-sectional view of the housing container according to the first exemplary embodiment of the present invention at the time of housing the organism sample measurement sensor.
Figure 5:
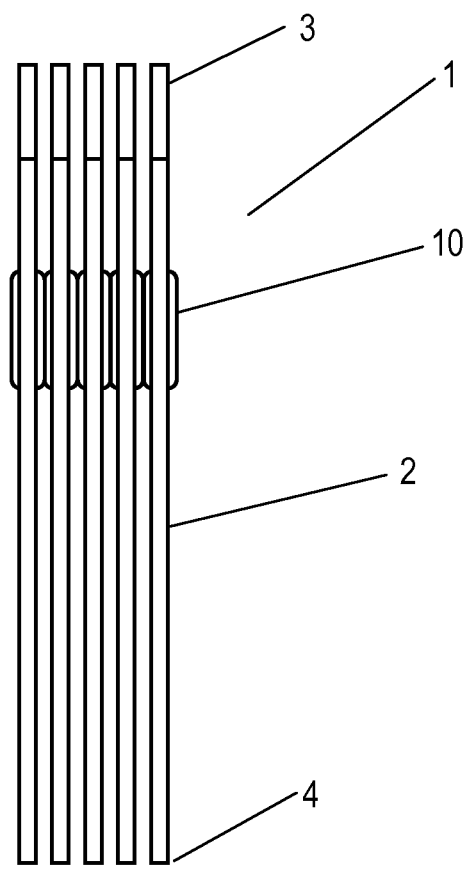
FIG. 5 is a side view of the organism sample measurement sensor housed in the housing container according to the first exemplary embodiment of the present invention.

A thickness of close contact prevention parts 10, that is, a thickness vertical to a surface of sensor body 2, is smaller than a thickness of sensor body 2 (e.g., 0.5 mm). More specifically, the thickness of close contact prevention parts 10 is substantially the same as a thickness of cover 8, and is approximately one-third of the thickness of sensor body 2. Since the thickness of close contact prevention parts 10 is smaller than the thickness of sensor body 2, as shown in FIG. 4, a large number of blood sugar level sensors 1 are housed in housing container 11 in FIG. 3. Housing container 11 includes housing container body 12 having a bottomed cylindrical shape and in which a top surface thereof is opened, and lid body 13 openably and closably covering an opening in the top surface of housing container body 12.

In this exemplary embodiment, close contact prevention parts 10 configured by plate-like bodies having substantially the same rectangular shape adhere into the same position of both the front surface and the back surface of sensor body 2. Therefore, sensor bodies 2 cannot come into close contact with each other in housing container body 12, so that a plurality of blood sugar level sensors 1 can be individually separated.

At this time, it is important that close contact prevention parts 10 having a rectangular shape be provided on both the front surface and the back surface of sensor body 2. For instance, when close contact prevention parts 10 are provided only on the front surfaces of sensor bodies 2 to abut the back surfaces of sensor bodies 2 onto each other, the entire back surfaces thereof come into close contact with each other to be difficult to be separated.

On the contrary, in this exemplary embodiment, close contact prevention parts 10 are provided on both the front surface and the back surface of sensor body 2. Therefore, even when the front surfaces or the back surfaces of sensor bodies 2 are abutted onto each other, sensor bodies 2 cannot come into close contact with each other in housing container body 12, so that blood sugar level sensors 1 can be individually separated.

As a result, a user can draw only one of individually separated blood sugar level sensors 1 out of housing container body 12 very easily.

This drawing-out will be specifically described. As shown in FIG. 6, close contact prevention parts 10 are provided in the position between the position of the center of gravity of sensor body 2 and measurement part 3, the position not overlapping with the position of the center of gravity of sensor body 2 and measurement part 3, that is, on a measurement part 3 side, and as shown in FIG. 4, blood sugar level sensor 1 is housed in housing container body 12 so that the measurement part 3 side is located toward the opening side of housing container body 12. Therefore, close contact prevention parts 10 on sensor body 2 of blood sugar level sensor 1 are arranged near the opening in the top surface of housing container body 12.

Therefore, the user can insert e.g., his/her forefinger from the opening of housing container body 12 to abut the inserted forefinger onto close contact prevention parts 10 near the opening.

Here, the length in the longitudinal direction of sensor body 2 of close contact prevention parts 10 is shorter. Since close contact prevention parts 10 are made smaller, the user lightly presses close contact prevention parts 10 in a direction of an inner wall surface of housing container body 12 with a cushion of the inserted forefinger to reliably catch close contact prevention parts 10. In addition, adjacent close contact prevention parts 10 that are made smaller can be prevented from coming into close contact with each other.

When sensor body 2 is moved by moving the forefinger from this state to the opening side of housing container body 12, each of individually separated blood sugar level sensors 1 can be drawn out of housing container body 12.

In addition, close contact prevention parts 10 are provided from end to end in the lateral direction of sensor body 2. Therefore, the user can draw out sensor body 2 by catching an end section on a connection terminal 4 side of either of close contact prevention parts 10 with the cushion of the inserted forefinger. The drawing-out ability of sensor body 2 can thus be enhanced.

As a result, the user can take one blood sugar level sensor 1 out of housing container body 12 very easily.

Such blood sugar level sensor 1 has been made smaller in recent years. Therefore, when blood sugar level sensor 1 is taken out of housing container body 12 to be set in the measurement device (not shown), blood sugar level sensor 1 can be accidentally dropped.

Accordingly, as shown in FIG. 6, in blood sugar level sensor 1 of this exemplary embodiment, close contact prevention parts 10 are provided in the position between the position of the center of gravity of sensor body 2 and measurement part 3, the position not overlapping with the position of the center of gravity of sensor body 2 and measurement part 3.

Therefore, for instance, sensor body 2 that is accidentally dropped onto a desk makes a line contact with a surface of the desk at connection terminal 4 and the end section on the connection terminal 4 side of either of close contact prevention parts 10. Then, by the line contact at two locations, sensor body 2 is tiltably held with respect to the surface of the desk. Therefore, sensor body 2 cannot come into close contact with the top surface of the desk.

To house a maximum number of blood sugar level sensors 1 in housing container 11, the thickness of close contact prevention parts 10 is smaller than the thickness of sensor body 2. This makes a gap between dropped sensor body 2 and the surface of the desk smaller, so that sensor body 2 is difficult to be taken up. Accordingly, in this exemplary embodiment, the line contact at two locations tiltably holds dropped sensor body 2 to forcefully lift an end section on the measurement part 3 side of sensor body 2.

By this lifting, the gap between the end section on the measurement part 3 side of sensor body 2 and the surface onto which sensor body 2 is dropped becomes larger. Therefore, the user can hold sensor body 2 between e.g., his/her fingers in the gap to easily take up sensor body 2.

At this time, since sensor body 2 only makes a line contact with the surface of the desk at two locations, the user can easily slide and move sensor body 2 to a place appropriate for taking up sensor body 2. Since close contact prevention parts 10 are provided on the front surface and the back surface of sensor body 2, even when either of the front surface and the back surface of dropped sensor body 2 is directed downward, blood sugar level sensor 1 can be handled in the same manner.

As a result, blood sugar level sensor 1 can be easily handled even after blood sugar level sensor 1 is taken out of housing container 11.

Further, opposite surfaces of close contact prevention parts 10 of this exemplary embodiment of surfaces thereof adhering onto sensor body 2, that is, surfaces thereof onto which the forefinger of the user is abutted, are rough surfaces. Therefore, the user can reliably catch the rough surfaces of close contact prevention parts 10 with the cushion of the inserted forefinger.

In the above description, close contact prevention parts 10 are configured by rectangular plate-like bodies, but, in place of that, close contact prevention parts 10 may be configured by printing. More specifically, even when close contact prevention parts 10 are configured by screen printing with silica gel in the same position on the front surface and the back surface of sensor body 2 on the measurement part 3 side between measurement part 3 and connection terminal 4, one blood sugar level sensor 1 can be drawn out of housing container body 12 very easily.

That is, by swelled printing ink, the front surfaces and the back surfaces of adjacent blood sugar level sensors 1 in which close contact prevention parts 10 are configured on the front surfaces and the back surfaces of sensor bodies 2 by screen printing can be prevented from coming into close contact with each other. Therefore, one blood sugar level sensor 1 can be easily taken out of housing container body 12.

When close contact prevention parts 10 are configured by screen printing with silica gel that is an example of a moisture absorber, measurement accuracy of blood sugar level sensor 1 can be prevented from being varied.

That is, measurement part 3 of blood sugar level sensor 1 reacts blood with the reagent to measure a blood sugar level, but moisture in air also reacts with the reagent. Consequently, when moisture prevention is insufficient at the time of housing blood sugar level sensor 1 in housing container 11, the measurement accuracy of blood sugar level sensor 1 can be varied.

Accordingly, in this exemplary embodiment, close contact prevention parts are configured by screen printing with silica gel, and to prevent moisture, close contact prevention parts 10 configured on blood sugar level sensor 1 by screen printing with silica gel absorb moisture in sealed housing container 11 that houses blood sugar level sensor 1.

As a result, the measurement accuracy of blood sugar level sensor 1 as the organism sample measurement sensor according to this exemplary embodiment can be prevented from being varied, and one blood sugar level sensor 1 can be taken out of housing container body 12 very easily.

Second Exemplary Embodiment

In the first exemplary embodiment of the present invention, the user inserts the forefinger into housing container 11 to take out blood sugar level sensor 1. In the second exemplary embodiment of the present invention, blood sugar level sensor 1 in housing container 11 is shakingly taken out.

Figure 7:
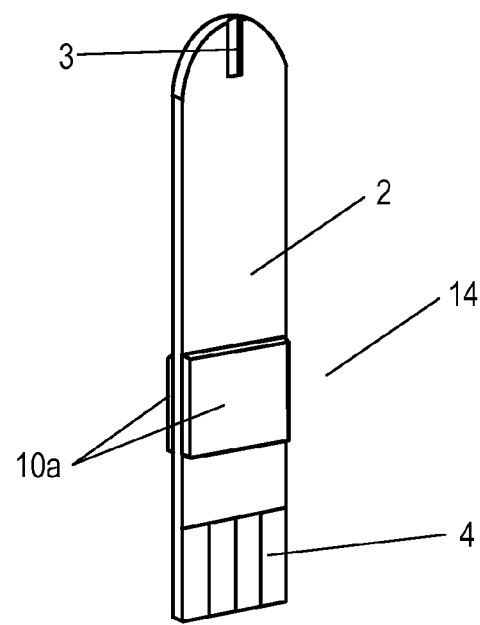
FIG. 7 is a perspective view of an organism sample measurement sensor according to a second exemplary embodiment of the present invention.

FIG. 7 shows the blood sugar level sensor according to this exemplary embodiment.

As shown in FIG. 7, blood sugar level sensor 14 as the organism sample measurement sensor according to this exemplary embodiment and blood sugar level sensor 1 according to the first exemplary embodiment have different mounted positions of close contact prevention parts.

Figure 12:
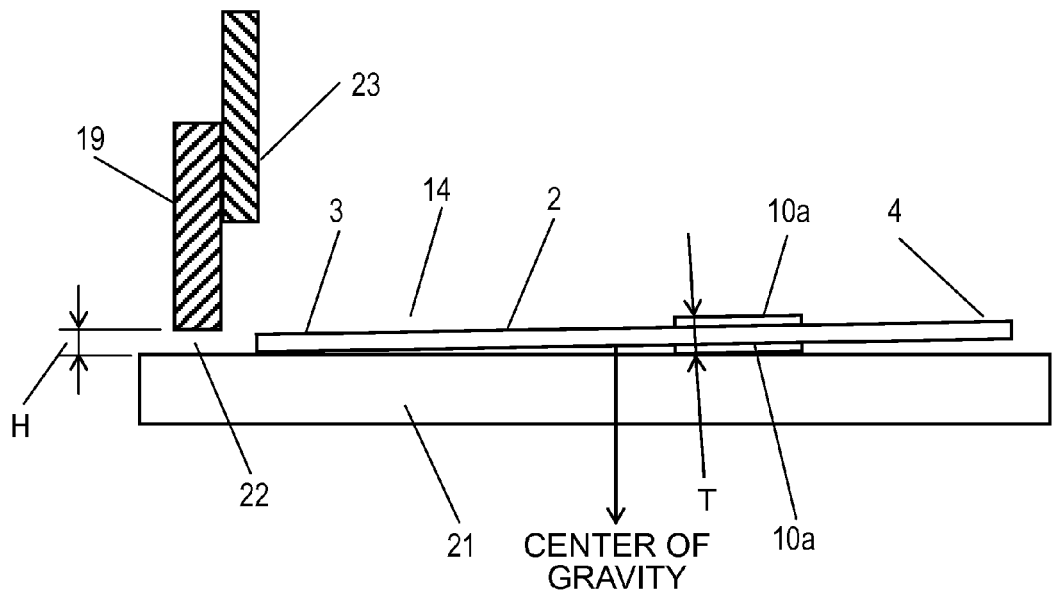
FIG. 12 is a cross-sectional view of an essential part of the housing container according to the second exemplary embodiment of the present invention.

Specifically, close contact prevention parts 10a configured by plate-like bodies are provided in a position between a position of a center of gravity of sensor body 2 and connection terminal 4, the position not overlapping with the position of the center of gravity of sensor body 2 and connection terminal 4. That is, as shown in FIG. 12, close contact prevention parts 10a are provided in the position between the position of the center of gravity of sensor body 2 and connection terminal 4 in a state where blood sugar level sensor 14 is laid sideways, the position not overlapping with the position of the center of gravity of sensor body 2 and connection terminal 4.

A housing container suitable for blood sugar level sensor 14 will be described below in detail.

Figure 8:
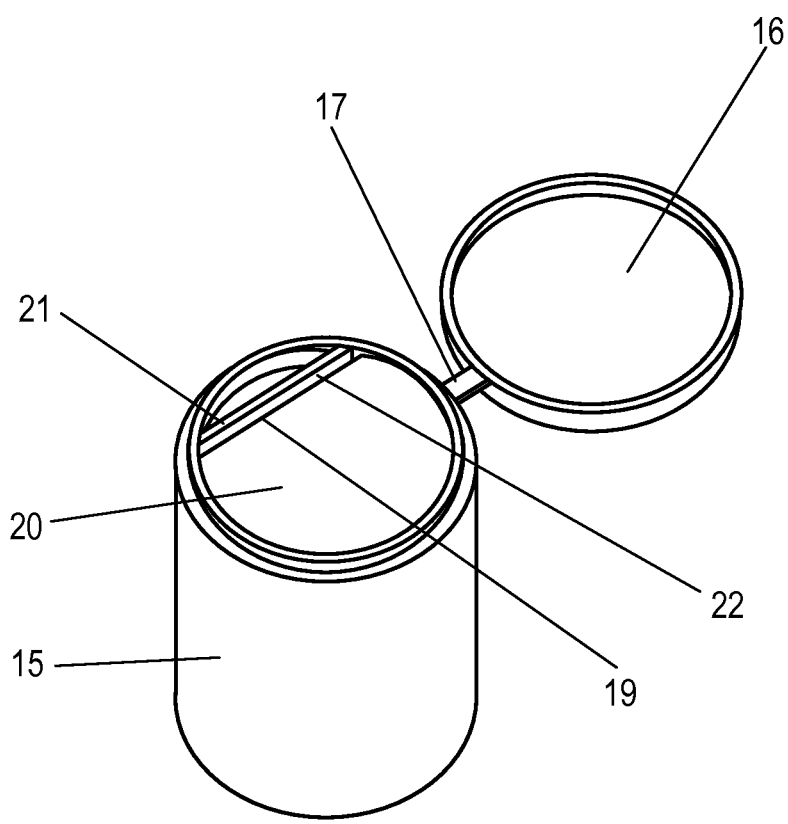
FIG. 8 is a perspective view of a housing container according to the second exemplary embodiment of the present invention.

As shown in FIG. 8, lid 16 is openably and closably provided along an edge of an opening of a top surface of container body 15 having a bottomed cylindrical shape and in which the top surface thereof is opened. Container body 15 and lid 16 are integrated with a synthetic resin, and are connected by connection part 17.

Figure 9:
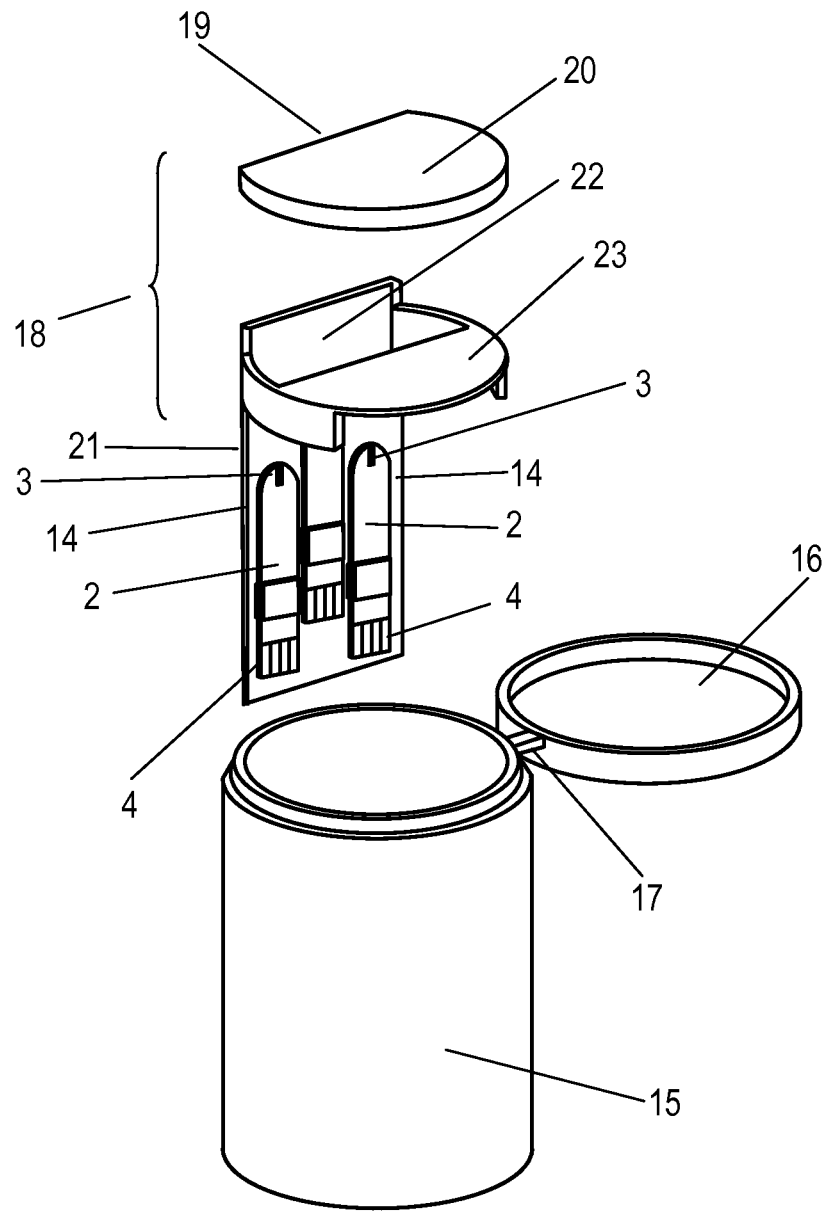
FIG. 9 is an exploded perspective view of the housing container according to the second exemplary embodiment of the present invention.

FIG. 9 is an exploded perspective view of the housing container according to this exemplary embodiment. Container body 15 includes therein shaking-out member 18 mounted on an upper side in container body 15, and blood sugar level sensor 14 having a long plate shape, housed in container body 15, and shaken out of container body 15 via shaking-out member 18.

Shaking-out member 18 shaking out blood sugar level sensor 14 has elastic top plate 20 made of rubber as an example of an elastic body, mounted in the opening of container body 15, and having shaking-out side 19 on an outer peripheral section thereof, and a guide wall 21 opposite to shaking-out side 19 of elastic top plate 20 and hung downward from the opposite section.

Elastic top plate 20 has a substantially circular shape according to the shape of the opening of the top surface of container body 15. As shown in FIG. 8, when shaking-out member 18 is housed in container body 15, elastic top plate 20 covers the opening in the top surface of container body 15.

Figure 10:
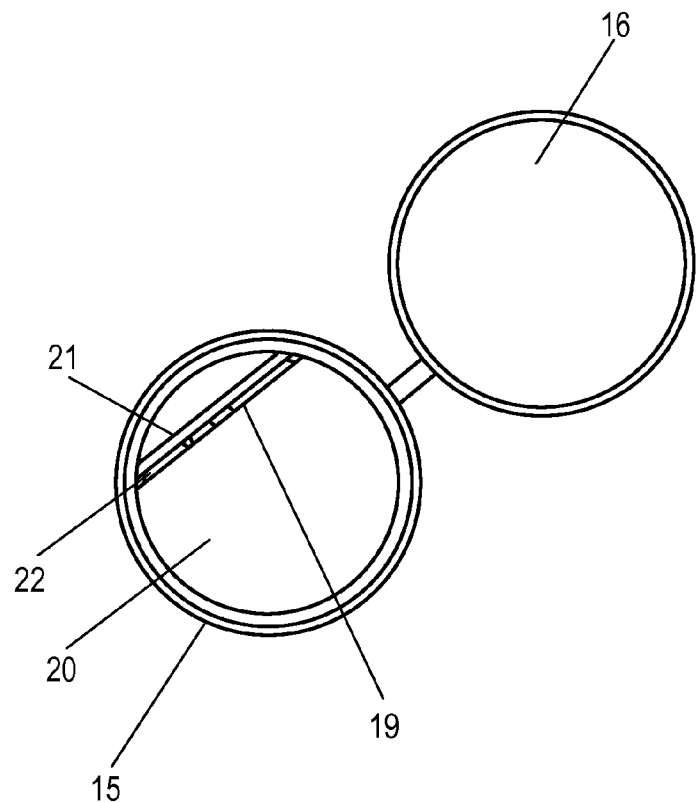
FIG. 10 is a top view of the housing container according to the second exemplary embodiment of the present invention.
Figure 13:
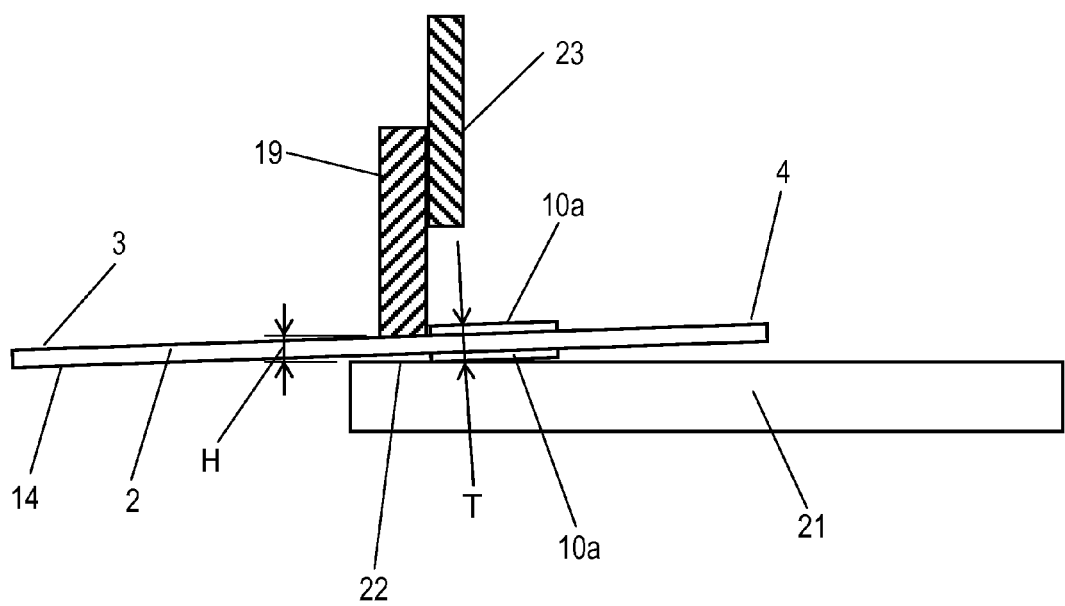
FIG. 13 is a cross-sectional view of the essential part of the housing container according to the second exemplary embodiment of the present invention.

As shown in FIGS. 8 and 10, in shaking-out member 18, shaking-out side 19 of elastic top plate 20 and guide wall 21 that are opposite to each other form shaking-out opening 22 that is horizontally long. As shown in FIGS. 12 and 13, short side shaking-out width H of a short side of shaking-out opening 22 (in FIGS. 12 and 13, a height in an up-down direction) is larger than a plate thickness of one sensor body 2 and is smaller than a plate thickness of two sensor bodies 2. Further, close contact prevention parts thickness T of a portion of sensor body 2 in which close contact prevention parts 10a are provided (a thickness from a front surface of sensor body 2 to a back surface thereof) is larger than short side shaking-out width H of shaking-out opening 22.

More specifically, short side shaking-out width H of shaking-out opening 22 is 1.3 times larger than the plate thickness of one sensor body 2, and close contact prevention parts thickness T of sensor body 2 is 1.6 times larger than the plate thickness of one sensor body 2. Thus, close contact prevention parts 10a on sensor body 2 can be caught into shaking-out opening 22, which will be described later in detail.

Close contact prevention parts thickness T of sensor body 2 is smaller than the plate thickness of two sensor bodies 2. More specifically, as described above, close contact prevention parts thickness T is 1.6 times larger than the plate thickness of one sensor body 2, and is smaller than the plate thickness of two sensor bodies 2. That is, close contact prevention parts thickness T is smaller to house a large number of blood sugar level sensors 14 in container body 15.

As shown in FIG. 9, guide wall 21 of shaking-out member 18 has a rectangular shape, and a length thereof in a longitudinal direction is longer than a length of sensor body 2. As shown in FIGS. 9 and 12, sensor body 2 can be placed on guide wall 21, and can be guided into shaking-out opening 22 at the time of shaking out blood sugar level sensor 14.

Further, both end sections in the longitudinal direction of guide wall 21 are abutted onto inner wall surfaces of container body 15. Therefore, vibration of guide wall 21 in container body 15 due to vibration of shaken-out blood sugar level sensor 14 can be prevented.

Guide wall 21 is provided with holding part 23 holding elastic top plate 20. Elastic top plate 20 adheres onto holding part 23 with e.g., a double-faced tape near the outer peripheral section thereof on the opposite side of shaking-out side 19. Therefore, shaking-out side 19 of elastic top plate 20 is elastically held in an axial direction of container body 15 about the adhering portion.

As shown in FIG. 9, blood sugar level sensor 14 extends along guide wall 21 of shaking-out member 18 so that measurement part 3 of sensor body 2 is located toward the upper side, that is, so that measurement part 3 is located toward shaking-out opening 22 that is horizontally long, and in this state, shaking-out member 18 is housed in container body 15. As shown in FIG. 8, elastic top plate 20 of shaking-out member 18 covers the opening of container body 15.

Then, when the user closes lid 16, lid 16 that covers elastic top plate 20 of shaking-out member 18 covers the opening in the top surface of container body 15. In this state, the user conveys container body 15 to an examining place.

An operation of the above configuration will be described below.

FIGS. 11 to 14 are explanatory views of a state where the user takes only one blood sugar level sensor 14 out of container body 15.

Figure 11:
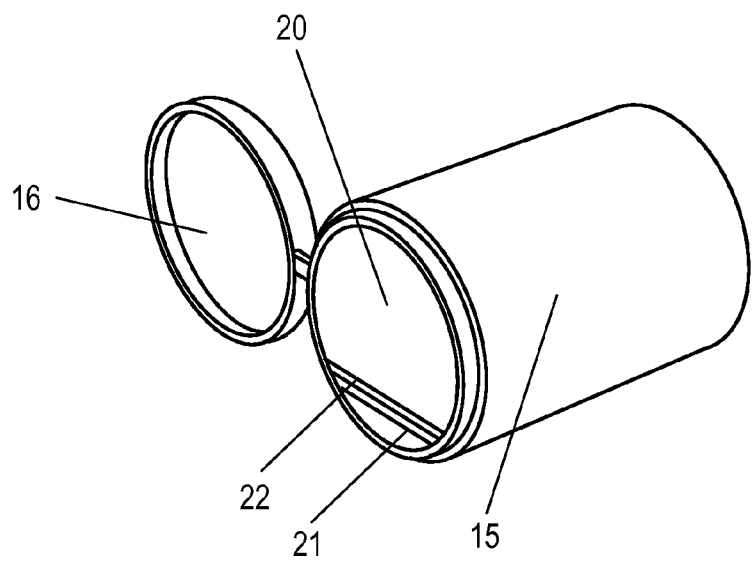
FIG. 11 is a perspective view of the housing container according to the second exemplary embodiment of the present invention at the time of shaking out an examination plate.
Figure 14:
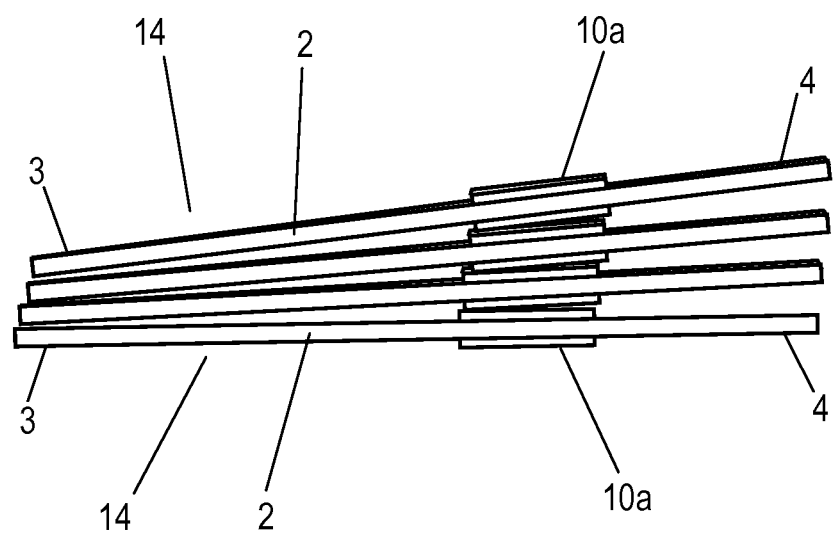
FIG. 14 is a side view of stacked organism sample measurement sensors according to the second exemplary embodiment of the present invention.
Figure 15:
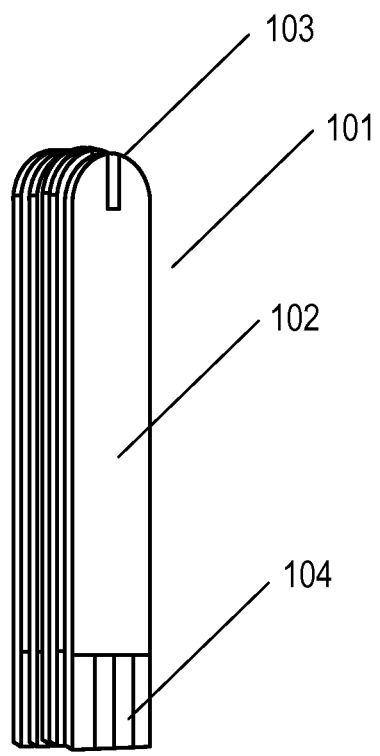
FIG. 15 is a perspective view of a blood sugar level sensor as a conventional organism sample measurement sensor housed in a housing container.

That is, as shown in FIG. 11, when the user takes only one blood sugar level sensor 14 out of container body 15, lid 16 is opened from container body 15 to lay container body 15 sideways. As shown in FIG. 12, sensor body 2 of blood sugar level sensor 14 in container body 15 is placed on a wall surface of guide wall 21. In this state, cylindrical container body 15 is shaken in a direction vertical to a longitudinal direction of container body 15 and in a horizontal direction, that is, to front and back sides in FIG. 12. As shown in FIG. 12, in container body 15, by the vibration, sensor body 2 of one blood sugar level sensor 14 is placed on guide wall 21 in a state where the front surface or the back surface thereof extends along the wall surface of guide wall 21. As shown in FIG. 14, a plurality of blood sugar level sensors 14 are overlapped and stacked on sensor body 2.

In this exemplary embodiment, close contact prevention parts 10a configured by plate-like bodies are provided in the same position of the front surface and the back surface on a connection terminal 4 side from a center in a longitudinal direction of sensor body 2, and close contact prevention parts 10a provided on the front surface and the back surface of sensor body 2 have substantially the same shape.

Therefore, in a state where a plurality of blood sugar level sensors 14 are housed in container body 15, close contact prevention parts 10a are present in the same position between overlapped blood sugar level sensors 14, so that sensor bodies 2 of blood sugar level sensors 14 can be prevented from coming into close contact with each other.

At this time, it is important that close contact prevention parts 10a configured by rectangular parallelepiped plate-like bodies be provided on both the front surface and the back surface of sensor body 2.

That is, for instance, when close contact prevention parts 10a are provided only on the front surfaces of sensor bodies 2 to abut the back surfaces of sensor bodies 2 onto each other, the back surfaces come into close contact with each other to be difficult to be separated. However, in this exemplary embodiment, close contact prevention parts 10a are provided on both the front surface and the back surface of sensor body 2.

Therefore, even when the front surfaces or the back surfaces of sensor bodies 2 of a plurality of blood sugar level sensors 14 are abutted onto each other, sensor bodies 2 cannot come into close contact with each other and can be easily individually separated.

Blood sugar level sensor 14 in FIG. 12 is the lowest one of stacked blood sugar level sensors 14 in FIG. 14.

As described above, in blood sugar level sensor 14 of this exemplary embodiment, close contact prevention parts 10a are provided in the position between the position of the center of gravity of sensor body 2 and connection terminal 4, the position not overlapping with the position of the center of gravity of sensor body 2 and connection terminal 4. Therefore, in a state where blood sugar level sensor 14 is laid sideways, a measurement part 3 side of blood sugar level sensor 14 is lowered toward shaking-out opening 22.

As shown in FIG. 13, when container body 15 is shaken from this state in the longitudinal direction of container body 15, that is, in a right-left direction in FIG. 13, one of stacked blood sugar level sensors 14 is slid on the wall surface of guide wall 21 to enter shaking-out opening 22.

As described above, in this exemplary embodiment, short side shaking-out width H of shaking-out opening 22 that is horizontally long is larger than the plate thickness of one sensor body 2, and is smaller than the plate thickness of two sensor bodies 2. Therefore, two overlapped sensor bodies 2 cannot enter shaking-out opening 22, so that only the lowest one of stacked blood sugar level sensors 14 can be taken out of container body 15.

As described above, in this exemplary embodiment, close contact prevention parts 10a can prevent sensor bodies 2 from coming into close contact with each other and can be easily separated. Therefore, only the lowest blood sugar level sensor 14 can easily enter shaking-out opening 22.

As a result, as shown in FIG. 13, the measurement part 3 side of sensor body 2 of blood sugar level sensor 14 that has entered shaking-out opening 22 exits out of container body 15.

As shown in FIG. 14, in this exemplary embodiment, the end sections on the measurement part 3 side of close contact prevention parts 10a are provided from one end section to the other end section in a direction orthogonal to the longitudinal direction of sensor body 2, that is, close contact prevention parts 10a cross the lateral direction of sensor body 2. Further, as shown in FIG. 13, close contact prevention parts thickness T of sensor body 2 is 1.6 times larger than the thickness of one sensor body 2, and is larger than short side shaking-out width H of shaking-out opening 22 that is 1.3 times larger than the thickness of one sensor body 2.

Therefore, the end sections on the measurement part 3 side of close contact prevention parts 10a are caught onto elastic top plate 20 in shaking-out opening 22. That is, close contact prevention parts 10a configured by plate-like bodies function as stoppers. As a result, blood sugar level sensor 14 becomes stationary in a state where measurement part 3 of sensor body 2 is projected out of container body 15 from shaking-out opening 22.

The user draws stationary sensor body 2 out of container body 15.

In this exemplary embodiment, elastic top plate 20 adheres onto holding part 23 with e.g., a double-faced tape near the outer peripheral section thereof on the opposite side of shaking-out side 19. Therefore, shaking-out side 19 of elastic top plate 20 is elastically held in the longitudinal direction of container body 15 about the adhering portion.

When the user draws blood sugar level sensor 14 out of container body 15, elastic top plate 20 is pushed by close contact prevention parts 10a to be slightly warped out of container body 15, so that sensor body 2 can be drawn out of container body 15.

As a result, the user can take one blood sugar level sensor 14 out of container body 15 very easily.

As shown in FIG. 11, in this exemplary embodiment, shaking-out opening 22 that is horizontally long is provided from one end section of guide wall 21 to the other end section thereof in the direction orthogonal to the longitudinal direction of guide wall 21. As shown in FIG. 9, sensor bodies 2 of a plurality of blood sugar level sensors 14 can be arranged in parallel on guide wall 21 toward shaking-out opening 22. As shown in FIG. 11, when container body 15 is lightly shaken in the longitudinal direction of container body 15, that is, in the right-left direction in FIG. 13, sensor bodies 2 arranged in parallel enter shaking-out opening 22, so that sensor bodies 2 of a plurality of blood sugar level sensors 14 become stationary to be projected out of container body 15.

Therefore, the user may draw out one of sensor bodies 2 that can be drawn out most easily. In this respect, a plurality of blood sugar level sensors 14 can be easily taken out of shaking-out opening 22 one by one.

In this exemplary embodiment, even last blood sugar level sensor 14 can be easily taken out. That is, conventionally, for instance, since the sensor body of last blood sugar level sensor that is shaken out of the container body does not have close contact resistance with respect to other sensor bodies, the sensor body can be vigorously jumped out of the container body.

However, as described above, in this exemplary embodiment, close contact prevention parts 10a are provided on sensor body 2. Therefore, close contact prevention parts 10a are caught onto elastic top plate 20 in shaking-out opening 22, so that sensor body 2 of blood sugar level sensor 14 is projected halfway out of container body 15 to be stationary. Therefore, even last blood sugar level sensor 14 cannot be jumped out of container body 15.

As a result, even last blood sugar level sensor 14 can be taken out of container body 15 very easily.

INDUSTRIAL APPLICABILITY

As described above, for instance, the present invention can be widely used as the organism sample sensor, such as the blood sugar level sensor, and the housing container that houses the same.

REFERENCE MARKS IN THE DRAWINGS 1, 14 blood sugar level sensor (organism sample measurement sensor)
2 sensor body
3 measurement part
4 connection terminal
5 connection part
6 substrate
7 spacer
8 cover
9 reagent
10, 10a close contact prevention part
11 housing container
12 housing container body
13 lid body
15 container body
16 lid
17 connection part
18 shaking-out member
19 shaking-out side
20 elastic top plate
21 guide wall
22 shaking-out opening
H short side shaking-out width
23 holding part
T close contact prevention parts thickness

The invention claimed is:
1. An organism sample measurement sensor comprising:
a sensor body formed into a long plate shape;
a measurement part provided in a front end section of the sensor body;

a connection terminal provided in a rear end section of the sensor body; and a connection part electrically connecting the measurement part and the connection terminal in the sensor body, wherein the sensor body has close contact prevention parts of an identical plate shape disposed to the same positions on both a front surface and a back surface respectively, the positions not overlapping with any of a center of gravity of the sensor body, the measurement part, and the connection terminal, and the close contact prevention parts have a length in a longitudinal direction of the sensor body shorter than a length in a direction orthogonal to the longitudinal direction of the sensor body.

2. The organism sample measurement sensor according to claim 1, wherein the close contact prevention parts are configured by a plate-like body.

3. The organism sample measurement sensor according to claim 2, wherein a thickness of the close contact prevention parts in a direction perpendicular to a surface of the sensor body is smaller than a thickness of the sensor body.

4. The organism sample measurement sensor according to claim 3, wherein the plate-like body configuring the close contact prevention parts has a rough surface on an opposite side to a side adhering to the sensor body.

5. The organism sample measurement sensor according to claim 1, wherein the close contact prevention parts are formed on the surfaces of sensor body by printing.

6. The organism sample measurement sensor according to claim 5, wherein the printing is screen printing.

7. The organism sample measurement sensor according to claim 6, wherein a moisture absorber is printed by the screen printing.

8. A housing container formed into a bottomed cylindrical shape and housing a plurality of organism sample measurement sensors according to claim 1.

9. The housing container according to claim 8, wherein an openable (and closeable) lid body is provided in an opening in a top surface of a housing container body.

10. A housing container comprising:
a container body of which a top surface is opened;
a shaking-out member mounted on an upper side of the container body; and the organism sample measurement sensor of the long plate shape according to claim 1 housed in the container body, and removable by being shaken out of the container body through the shaking-out member, wherein the shaking-out member has an elastic top plate mounted to an opening of the container body and having a shaking-out side on an outer peripheral section thereof, and a guide wall provided in an opposite section to the shaking-out side of the elastic top plate and extended downward from the opposite section, and the shaking-out side and the guide wall that are opposite to each other form a laterally elongated shaking-out opening so that a short side width of the shaking-out opening is larger than a thickness of one sensor body of the organism sample measurement sensor but smaller than a total thickness of two sensor bodies.

11. The housing container according to claim 10, wherein a thickness of the sensor body where the close contact prevention parts are provided is larger than the short side width of the shaking-out opening.

12. The housing container according to claim 10, wherein a thickness of the sensor body where the close contact prevention parts are provided is smaller than the total thickness of two sensor bodies.

13. The housing container according to claim 10, wherein the guide wall has a rectangular shape, and a length of the guide wall in a longitudinal direction is longer than a length of the sensor body.

14. The housing container according to claim 13, wherein the guide wall is provided with a holding part holding the elastic top plate.

15. The housing container according to claim 14, wherein both end sections along the longitudinal direction of the guide wall are abutted to respective portions of an inner wall surface of the container body.

16. The housing container according to claim 10, wherein the shaking-out opening is provided from one end section to the other end section of the guide wall in a direction orthogonal to the longitudinal direction of the guide wall.

17. The housing container according to claim 10, wherein a lid is provided on an upper side of the opening for openably covering the elastic top plate of the shaking-out member and the opening.

* * * * *